(12) United States Patent
Park et al.

(10) Patent No.: US 10,815,312 B2
(45) Date of Patent: *Oct. 27, 2020

(54) BIFUNCTIONAL PEPTIDE HAVING CAPABILITY TO PERMEATE CELLS AND CAPABILITY TO REGENERATE MUSCLES AND USE THEREOF

(71) Applicants: Seoul National University R&DB Foundation, Seoul (KR); Nano Intelligent Biomedical Engineering Corporation Co. Ltd., Chungcheongbuk-do (KR)

(72) Inventors: Yoon Jeong Park, Seoul (KR); Chong-Pyoung Chung, Seoul (KR); Jue-Yeon Lee, Gyeonggi-do (KR)

(73) Assignees: SEOUL NATIONAL UNIVERSITY R&DB FOUNDATION, Seoul (KR); NANO INTELLIGENT BIOMEDICAL ENGINEERING CORPORATION CO. LTD., Chungcheongbuk-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,864

(22) Filed: Mar. 11, 2019

(65) Prior Publication Data

US 2019/0284306 A1 Sep. 19, 2019

(30) Foreign Application Priority Data

Mar. 14, 2018 (KR) ........................ 10-2018-0029913

(51) Int. Cl.
| | |
|---|---|
| A61K 35/34 | (2015.01) |
| A61K 38/10 | (2006.01) |
| A61K 9/00 | (2006.01) |
| C07K 7/08 | (2006.01) |
| C07K 19/00 | (2006.01) |
| A61P 21/00 | (2006.01) |
| A61L 27/54 | (2006.01) |
| A61L 27/22 | (2006.01) |

(52) U.S. Cl.
CPC ............ *C07K 19/00* (2013.01); *A61K 9/0014* (2013.01); *A61K 9/0019* (2013.01); *A61K 9/0053* (2013.01); *A61K 35/34* (2013.01); *A61K 38/10* (2013.01); *A61L 27/222* (2013.01); *A61L 27/225* (2013.01); *A61L 27/54* (2013.01); *A61P 21/00* (2018.01); *A61L 2430/30* (2013.01)

(58) Field of Classification Search
CPC ...... A61K 35/34; A61K 38/10; A61K 9/0014; A61K 9/0019; A61K 9/0053; A61K 9/00; A61L 2430/30; A61L 27/222; A61L 27/225; A61L 27/54; A61P 21/00; C07K 7/08; C07K 19/00

USPC ................. 514/12.1, 21.5, 1.1; 530/326, 300
See application file for complete search history.

(56) References Cited

U.S. PATENT DOCUMENTS

| 10,066,212 B2 * | 9/2018 | Park ................... C07K 14/4723 |
| 2010/0016232 A1 | 1/2010 | Kjaer et al. |
| 2012/0282228 A1 | 11/2012 | Bhasin |
| 2017/0275594 A1 | 9/2017 | Park et al. |

FOREIGN PATENT DOCUMENTS

| EP | 3111951 A1 | 1/2017 |
| KR | 101693533 B1 | 1/2017 |
| KR | 20170017385 A | 2/2017 |

OTHER PUBLICATIONS

Duchenne Muscular Dystrophy and Becker Muscular Dystrophy from Merck Manual, pp. 1-3. Accessed Mar. 19, 2020. (Year: 2020).*
Other Forms of Muscular Dhystrophy from Merck Manual, pp. 1-4. Accessed Mar. 19, 2020. (Year: 2020).*
Spinal Muscular Atrophies from Merck Manual, pp. 1-2. Accessed Mar. 19, 2020. (Year: 2020).*
Autoimmune Myositis from Merck Manual, pp. 1-7. Accessed Mar. 19, 2020. (Year: 2020).*
Peripheral Arterial Disease from Merck Manual, pp. 1-7. Accessed Mar. 19, 2020. (Year: 2020).*
Heart Failure from Merck Manual, pp. 1-21. Accessed Mar. 19, 2020. (Year: 2020).*
Kin, S., et al., "Regeneration of Skeletal Muscle Using In Situ Tissue Engineering on an Acellular Collagen Sponge in a Rabbit Model", "ASAIO Journal", 2007, pp. 506-513.
Guttsches, A., et al., "Human Beta-Defensin-3 Correlates with Muscle Fibre Degeneration in Idiopathic Inflammatory Myopathies", "Innate Immunity", 2014, pp. 49-60, vol. 20, No. 1.
Lee, J.Y., et al., "Identification of a Cell-Penetrating Peptide Domain From Human Beta-Defensin 3 and Characterization of its Inflammatory Activity", "International Journal of Nanomedicine", 2015, pp. 5423-5434, vol. 10.
Lu, A., et al., "NF-kB Negativity Impacts the Myogenic Potential of Muscle-Derived Stem Cells", "Molecular Therapy", 2012, pp. 661-668, vol. 20, No. 3.

(Continued)

*Primary Examiner* — Julie Ha
(74) *Attorney, Agent, or Firm* — Hultquist, PLLC; Steven J. Hultquist (57) ABSTRACT

Disclosed are a bifunctional peptide having the capability to permeate cells and the capability to regenerate muscles and the use thereof. Advantageously, the bifunctional peptide has a function of regenerating muscle cells and thus is useful for the prevention or treatment of diseases affecting muscle regeneration, and additionally has the capability to permeate cells and thus eliminates the necessity to adhere an additional peptide or add other agent or drug for cell permeation of the peptide, thereby finally exerting an efficient muscle generation effect. Thus, the bifunctional peptide can be easily applied to various surgical regenerative treatments and can shorten the treatment period.

5 Claims, 4 Drawing Sheets
(3 of 4 Drawing Sheet(s) Filed in Color)

Specification includes a Sequence Listing.

(56) References Cited

OTHER PUBLICATIONS

Mourkioti, F., et al., "NF-kB Signaling in Skeletal Muscle: Prospects for Intervention in MuscleDiseases", "J. Mol. Med.", 2008, pp. 747-759, vol. 86.
Remington, J.P., "Remington's Pharmaceutical Science", "17th Edition", 1985, pp. 1409-1677,17th Edition, Publisher: Mack Publishing Company, Easton, PA.

\* cited by examiner

Fig.4 ved. Regulation of appropriate HDACs is important to control normal development stages and the development of diseases. The roles of HDACs in treating a variety of diseases, including cancer, inflammatory diseases and degenerative diseases including neuropathy, and modulators thereof have been studied.
BIFUNCTIONAL PEPTIDE HAVING CAPABILITY TO PERMEATE CELLS AND CAPABILITY TO REGENERATE MUSCLES AND USE THEREOF

CROSS-REFERENCE TO RELATED APPLICATION

The priority under 35 USC 119 of Korean Patent Application No. 10-2018-0029913 filed Mar. 14, 2018 is hereby claimed. The disclosure of Korean Patent Application No. 10-2018-0029913 is hereby incorporated herein by reference in its entirety, for all purposes.

TECHNICAL FIELD

The present invention relates to a bifunctional peptide having the capability to permeate cells and the capability to regenerate muscles and the use thereof. More particularly, the present invention relates to a pharmaceutical composition for preventing or treating a muscle disease and a tissue-engineering scaffold for treating a muscle disease comprising a peptide represented by an amino acid sequence of any one of SEQ ID NOS: 1 to 8.

BACKGROUND ART

Although skeletal muscle is capable of self-regeneration, increased tissue damage due to trauma, congenital defects, senile dementia or tumor resection requires a surgical approach such as surgery, and a method of injecting autologous or allograft myoblasts or gene medicine into muscles is used.

When muscle stem cells and muscles are damaged, myoblasts, involved in regeneration, are known to be separated from some of muscle satellite cells. The satellite cells are positioned between the basement membrane and the membrane surrounding the muscle fiber surface of the muscle. Satellite cells are present in the basement membrane in a resting phase, but synthesize proteins through division and proliferation processes, and return to the resting satellite cells to thus maintain the cell number when muscles are damaged by external stimuli or stress. Satellite cells are widely used in muscle regeneration therapy. Satellite cells can be obtained by culturing a large amount of cells in a short period of time, can easily transfer genes to viruses or other vectors, and differentiate into muscular cells and stop growing upon intercellular contact, and there is no risk of transformation thereof into cancer cells due to overexpression, and thus the possibility of utilization thereof for tissue engineering is promising.

In order to treat a wide range of skeletal muscle defects, implantation of stem cells derived from skeletal muscle such as satellite cells that directly differentiate into muscle fibers or tissue engineering methods using cells and scaffolds have been attempted. However, it has been reported that stem cells and satellite cells can be grown in vitro, but have low proliferation, differentiation and regeneration ability due to the short culture period when injected into muscles.

The paper published by Kin et al in 2007 showed that, unlike a control group, scar tissue and new muscle tissue were formed when collagen scaffolds were transplanted into the wound site of rabbit leg skeletal muscle (Shuichi Kin, et al., Regeneration of Skeletal Muscle Using In-Situ Tissue Engineering on an Acellular Collagen Sponge Scaffold in a Rabbit Model, ASAIO Journal 2007.). As a result of observation of permeated cells after implantation of PLA (poly-lactic acid) scaffolds into muscle tissue for an experiment on an in-situ regeneration approach in skeletal muscle tissue, muscle satellite cells and precursor cells expressing Pax3, Pax7, MyoD and the like were found, and an increase in the number of muscle cells permeating the scaffold upon treatment with a growth factor of IGF-1 was identified.

However, protein growth factors have a short half-life and have drawbacks of induction of tumors and side effects due to multifunctionality in consideration of commercialization. In order to overcome these problems, there is a need for a technology of stem cell differentiation by a substance selectively controlling the same using a welfare genetic molecular target.

Histone deacetylase (HDAC) is an enzyme that deacetylates histones to condense chromatin and inhibit gene transcription. A histone protein is an element that constitutes the nucleosome with DNA. The structure of the histone protein can be variously modified. Histone acetylation and methylation, along with DNA methylation, are important acquired mechanisms to regulate the expression of certain genes. In general, when the expression of the certain genes is activated, the histone tail is acetylated by a histone acetyltransferase (HAT), whereas when the histone tail is deacetylated by a histone deacetylase, i.e., HDAC, the expression of certain genes is inactivated, that is, gene expression is inhibited. Regulation of appropriate HDACs is important to control normal development stages and the development of diseases. The roles of HDACs in treating a variety of diseases, including cancer, inflammatory diseases and degenerative diseases including neuropathy, and modulators thereof have been studied.

Previous studies have shown that HDAC inhibitors are effective not only in treating inflammation, but also in facilitating specific differentiation of stem cells into nerve, bone and liver tissues. However, there are no peptide-based HDAC inhibitors other than low-molecular-weight synthetic substances and inherited substances such as siRNA.

Accordingly, as a result of intensive studies to solve the problems of the prior art as described above, the present inventors have found a specific bifunctional peptide, which is capable of permeating cells and is capable of regenerating muscle cells by inhibiting the expression of HDAC and facilitating the differentiation of stem cells into myocytes, and have completed the present invention on the basis thereof.

DISCLOSURE

Technical Problem

Therefore, it is one object of the present invention to provide a pharmaceutical composition for preventing or treating a muscle disease comprising, as an active ingredient, a bifunctional peptide having the capability to permeate cells and the capability to regenerate muscles.

It is another object of the present invention to provide a tissue-engineering scaffold for treating a muscle disease comprising the bifunctional peptide.

Technical Solution

In accordance with the present invention, the above and other objects can be accomplished by the provision of a pharmaceutical composition for preventing or treating a muscle disease comprising, as an active ingredient, a bifunctional peptide represented by an amino acid sequence of any one of SEQ ID NOS: 1 to 8.

In accordance with another aspect of the present invention, provided is a tissue-engineering scaffold for treating a muscle disease comprising the bifunctional peptide.

In accordance with another aspect of the present invention, provided is a method for preventing or treating muscle disease comprising administering to the subject the bifunctional peptide.

In accordance with another aspect of the present invention, provided is a method for preventing or treating muscle disease using a tissue-engineering scaffold comprising the bifunctional peptide.

In accordance with another aspect of the present invention, provided is the bifunctional peptide for use in a method of preventing or treating muscle disease.

In accordance with another aspect of the present invention, provided is a pharmaceutical composition comprising the bifunctional peptide for use in a method of preventing or treating muscle disease.

In accordance with another aspect of the present invention, provided is a tissue-engineering scaffold comprising the bifunctional peptide for use in a method of preventing or treating muscle disease.

In accordance with another aspect of the present invention, provided is a use of the bifunctional peptide for the manufacture of a medicament for preventing or treating muscle disease.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and other objects, features and other advantages of the present invention will be more clearly understood from the following detailed description taken in conjunction with the accompanying drawings, in which.

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

In the present invention, the experiment was carried out by preparing a bifunctional peptide having the capability to permeate cells and the capability to regenerate muscle, and then treating muscle precursor cells and mesenchymal stem cells (MSCs) with the bifunctional peptide. As a result, it was found that the bifunctional peptide permeated cells, the expression of HDAC5 was reduced and the expression of marker proteins of muscle cells was increased.

Accordingly, in one aspect, the present invention is directed to a pharmaceutical composition for preventing or treating a muscle disease comprising, as an active ingredient, a peptide represented by an amino acid sequence of any one of SEQ ID NOS: 1 to 8.

SEQ ID NO: 1:
GKCSTRGRKCCRRKK

SEQ ID NO: 2:
GKCSTRGRKCMRRKK

SEQ ID NO: 3:
GKCSTRGRKMCRRKK

SEQ ID NO: 4:
GKCSTRGRKMMRRKK

SEQ ID NO: 5:
GKMSTRGRKCCRRKK

SEQ ID NO: 6:
GKMSTRGRKMCRRKK

SEQ ID NO: 7:
GKMSTRGRKCMRRKK

SEQ ID NO: 8:
GKMSTRGRKMMRRKK

In the present invention, SEQ ID NO: 2 is obtained by substituting cysteine of SEQ ID NO: 1 with methionine, wherein such substitution aims at preventing oxidation in the SS bond present in adjacent cysteine-cysteine or distant cysteine-cysteine structures. The total number of cysteines in SEQ ID NO: 1 is 3, and SEQ ID NOS: 2 to 8 are obtained by substituting these cysteines with methionine.

In the present invention, the peptide may have dual functions including the capability to permeate cells and the capability to regenerate muscle.

In the present invention, the peptide is preferably produced through a solid-phase peptide synthesis, when taking into consideration the fact that the peptide can be produced in a large amount compared to a protein produced by a recombinant DNA technique, but the present invention is not limited thereto.

Meanwhile, the present inventors have found through in-vitro experiments that the peptide can permeate cells and regenerate muscles.

In one embodiment of the invention, the bifunctional peptide is represented by an amino acid sequence that can permeate cells. Conventionally used antisense oligonucleotides have no capability to permeate cells. Therefore, in order to inhibit expression by binding to intracellular HDAC5, viral or nonviral gene carriers should be used, but such nonviral carriers have limited practical clinical applicability in consideration of safety. However, since the peptide according to the present invention has the intrinsic ability to permeate cells, there is no need to use additional carriers.

As used herein, the term "composition" is considered to include any product containing a certain ingredient as well as any product that is prepared directly or indirectly from a combination of certain ingredients.

In the present invention, the composition may further contain a pharmaceutically acceptable carrier, wherein the carrier is selected from the group consisting of saline, sterilized water, Ringer's solution, buffered saline, dextrose solution, maltodextrin solution, glycerol and ethanol, but the present invention is not limited thereto.

In the present invention, the composition may further contain at least one adjuvant selected from the group consisting of an excipient, a buffer, an antimicrobial antiseptic, a surfactant, an antioxidant, a tonicity adjuster, a preservative, a thickener and a viscosity modifier, but the present invention is not limited thereto. Each ingredient can be selected from a raw material commonly used in the art, and can be suitably modified and used within the range acceptable for the art.

In the present invention, the composition may be formulated into any one selected from the group consisting of a preparation for oral administration, a preparation for injection or a gel for topical implantation, but the present invention is not limited thereto, and can be prepared into a suitable formulation using a method well-known in the art (Joseph Price Remington, Remington's Pharmaceutical Science, 17th edition, Mack Publishing Company, Easton. Pa.).

In the present invention, the composition may be administered through a route commonly used in the pharmaceutical field, preferably parenteral administration, for example, intramuscular administration.

In the present invention, the term "active ingredient" generally means that the bifunctional peptide having cell permeability and muscle regeneration ability according to the present invention is contained as an active ingredient in a therapeutically effective amount.

In the present invention, the term "muscle disease" refers to any disease in which muscle tissue is lost due to damage to muscle tissue or muscle cells, and the term "composition for preventing or treating muscle disease" is used interchangeably with the term "composition for regenerating muscles".

In the present invention, the muscle disease is selected from the group consisting of muscular dystrophy, muscular atrophy, muscular sarcopenia, myositis, polymyositis, peripheral vascular disease and fibrosis, but the present invention is not limited thereto.

In the present invention, the term "treatment" includes: (a) inhibiting the development of a disease, disorder or symptoms; (b) alleviating a disease, disorder or symptoms; or (c) eliminating the disease, disease or symptoms.

In the present invention, the composition may be used as a therapeutic pharmaceutical composition itself to facilitate the differentiation of endogenous autologous stem cells, may be administered together with therapeutic graft stem cells and thus be used as a cell therapy adjuvant for differentiating grafted cells into muscle cells in a lesion site, or may be incorporated in an internal or external part of a polymer scaffold used for application of stem cells and thus may be released under control to regulate the function of the stem cells, but the present invention is not limited thereto.

In the present invention, the composition is preferably administered at a dose of 0.001 to 1,000 mg, more preferably 0.1 to 100 mg, per 1 kg of a body weight of the subject in need of treatment, but the present invention is not limited thereto, and the range of the dose may vary according to body weight, age, gender, state of health and diet of a patient, administration time, administration method, excretion rate and severity of disease. The dose can be determined in consideration of these factors by an ordinary expert in the art.

In another aspect, the present invention is directed to a method for preventing or treating muscle disease comprising administering to the subject the bifunctional peptide.

In another aspect, the present invention is directed to a method for preventing or treating muscle disease comprising administering to the subject a pharmaceutical composition comprising the bifunctional peptide.

In another aspect, the present invention is directed to a method for preventing or treating muscle disease using a tissue-engineering scaffold comprising the bifunctional peptide.

In another aspect, the present invention is directed to the bifunctional peptide for use in a method of preventing or treating muscle disease.

In another aspect, the present invention is directed to a pharmaceutical composition comprising the bifunctional peptide for use in a method of preventing or treating muscle disease.

In another aspect, the present invention is directed to a use of the bifunctional peptide for preventing or treating muscle disease.

In another aspect, the present invention is directed to a use of the bifunctional peptide for the manufacture of a medicament for preventing or treating muscle disease.

In another aspect, the present invention is directed to a tissue-engineering scaffold for treating a muscle disease comprising the bifunctional peptide.

In the present invention, the tissue-engineering scaffold is composed of a biological synthetic polymer capable of supporting cells, and may include an injection-type scaffold or a two- or three-dimensional scaffold, but the present invention is not limited thereto. The injection-type scaffold may load or may not load stem cells in a semi-solid state and the material thereof may be selected from the group consisting of collagen, gelatin, fibrin gel, alginate and hyaluronic acid, but the present invention is not limited thereto. Two- or three-dimensional scaffolds were prepared by casting a collagen-based scaffold, collagen or a synthetic polymer obtained by decellularization of a biological organ (myocardial membrane, pericardial membrane, or the like), imparting directionality to the result by nanopatterning or the like, and loading the peptide on the result, but the present invention is not limited thereto.

Hereinafter, the present invention will be described in more detail with reference to the following examples. However, it will be obvious to those skilled in the art that these examples are provided only for illustration of the present invention and should not be construed as limiting the scope of the present invention.

Example 1: Synthesis of Bifunctional Peptide Having Capability to Permeate Cells and Capability to Regenerate Muscles The peptide of SEQ ID NO: 1 was synthesized from the C terminal through F-moc solid-phase peptide synthesis using a synthesizer. That is, synthesis was performed using, as a blocking group, a Rink resin (0.075 mmol/g, 100 to 200 mesh, 1% DVB crosslinking) linked to Fmoc-(9-fluorenyl-methoxycarbonyl), and 50 mg of a Rink amide MBHA resin was added to the synthesizer and swollen with DMF, and a 20% piperidine/DMF solution was used to remove the Fmoc-group. A 0.5M amino acid solution (solvent: DMF), 1.0M DIPEA (solvent: DMF & NMP) and 0.5M HBTU (solvent: DMF) were added at 5, 10 and 5 equivalents, respectively, in accordance with the sequence from the C-terminal, and reacted under a stream of nitrogen for 1 to 2 hours. Whenever the deprotection and coupling steps were finished, the reaction solution was washed twice with DMF and methanol. After the last amino acid was coupled as well, the Fmoc-group was removed by deprotection.

The synthesis was identified by a ninhydrin test method. After the tested and completely synthesized resin was dried, Reagent K cleavage cocktail was added in an amount of 20 ml with respect to 1 g of the resin, and the resulting mixture was shaken for 3 hours and filtered to separate the resin from the cocktail in which the peptide was dissolved. Cold ether was added to the solution filtered through a filter to crystallize the peptide into a solid phase, which was then separated by centrifugation. At this time, the reagent K cleavage cocktail was completely removed by washing several times with ether and centrifugation. The crude product thus obtained was dissolved in distilled water and isolated and purified by liquid chromatography. The purified peptide was subjected to lyophilization.

SEQ ID NO: 1:
GKCSTRGRKCCRRKK

The peptide of SEQ ID NO: 2, in which the C-terminal fifth cysteine of the peptide of SEQ ID NO: 1 was substituted with methionine, was synthesized by an F-moc solid-phase chemical synthesis method using a synthesizer.

SEQ ID NO: 2:
GKCSTRGRKCMRRKK

The peptide of SEQ ID NO: 3, in which the C-terminal sixth cysteine of the peptide of SEQ ID NO: 1 was substituted with methionine, was synthesized by an F-moc solid-phase chemical synthesis method using a synthesizer.

SEQ ID NO: 3:
GKCSTRGRKMCRRKK

The peptide of SEQ ID NO: 4, in which the C-terminal fifth and sixth cysteines of the peptide of SEQ ID NO: 1 were substituted with methionine, was synthesized by an F-moc solid-phase chemical synthesis method using a synthesizer.

SEQ ID NO: 4:
GKCSTRGRKMMRRKK

The peptide of SEQ ID NO: 5, in which the N-terminal third cysteine of the peptide of SEQ ID NO: 1 was substituted with methionine, was synthesized by an F-moc solid-phase chemical synthesis method using a synthesizer.

SEQ ID NO: 5:
GKMSTRGRKCCRRKK

The peptide of SEQ ID NO: 6, in which the N-terminal third cysteine and the C-terminal sixth cysteine of the peptide of SEQ ID NO: 1 were substituted with methionine, was synthesized by an F-moc solid-phase chemical synthesis method using a synthesizer.

SEQ ID NO: 6:
GKMSTRGRKMCRRKK

The peptide of SEQ ID NO: 7, in which the N-terminal third cysteine and the C-terminal fifth cysteine of the peptide of SEQ ID NO: 1 were substituted with methionine, was synthesized by an F-moc solid-phase chemical synthesis method using a synthesizer.

SEQ ID NO: 7:
GKMSTRGRKCMRRKK

The peptide of SEQ ID NO: 8, in which the N-terminal third cysteine and the C-terminal fifth and sixth cysteines of the peptide of SEQ ID NO: 1 were substituted with methionine, was synthesized by an F-moc solid-phase chemical synthesis method using a synthesizer.

SEQ ID NO: 8:
GKMSTRGRKMMRRKK

The peptide of SEQ ID NO: 9 was produced as a control group of the peptides of SEQ ID NOS: 1 to 8 by an F-moc solid-phase chemical synthesis method using a synthesizer.

SEQ ID NO: 9:
GLRSKSKKFRRPDIQYPDA

Figure 1:
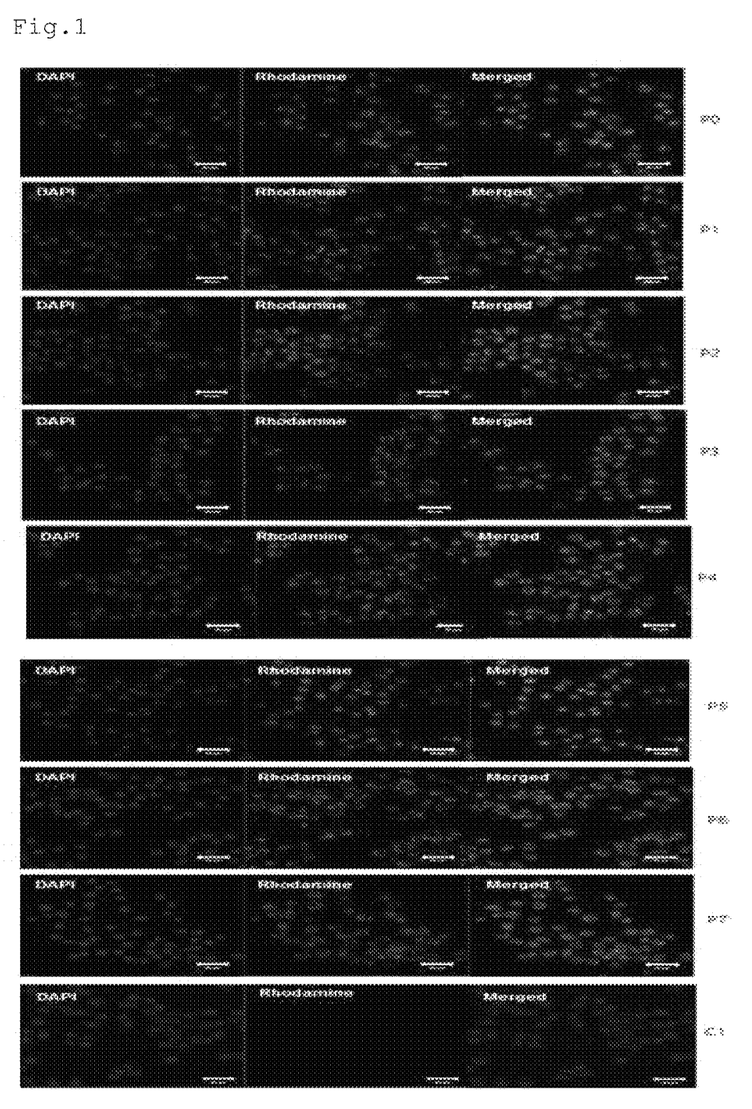
FIG. 1 shows the result of analysis with a confocal microscope to identify the degree of intracellular permeability 10 minutes after treating muscle precursor cells (C2C12) with the peptides of SEQ ID NOS: 1 to 8 and the control peptide of SEQ ID NO: 9 (SEQ ID NO: 1: P0, SEQ ID NO: 2:P1, SEQ ID NO: 3: P2, SEQ ID NO: 4: P3, SEQ ID NO: 5: P4, SEQ ID NO: 6: P5, SEQ ID NO: 7: P6, SEQ ID NO: 8: P7, SEQ ID NO: 9: C1).

Test Example 1: Evaluation of Cell Permeability of Bifunctional Peptide Having Capability to Permeate Cells and Capability to Regenerate Muscles Muscle precursor cells (C2C12) were transplanted at a density of $1.5 \times 10^5$/well in a 6-well plate and cultured in EMEM (Eagle's Minimal Essential Medium, ATCC). The medium was replaced at 24-hour intervals until confluency of cells reached 50%. When the confluency was 50%, the medium was replaced with Essential 8 medium, and the cells were treated with 10 µM of peptides of SEQ ID NOS: 1 to 8 labeled with rhodamine and 10 µM of control peptide (SEQ ID NO: 9), respectively. 10 minutes later, the cells were immobilized and observed with a confocal microscope. It was found that the peptides of SEQ ID NOS: 1 to 8 permeated cells, in contrast to the control peptide (SEQ ID NO: 9) (FIG. 1).

Test Example 2: Evaluation of Inhibition of HDCA5 Expression by Bifunctional Peptide Having Capability to Permeate Cells and Capability to Regenerate Muscles Muscle precursor cells (C2C12) were transplanted at a density of $1.5 \times 10^6$/well in a 10 pi dish and cultured in EMEM (Eagle's Minimal Essential Medium, ATCC). The medium was replaced at 24-hour intervals until confluency of cells reached 50%. When the confluency was 50%, the medium was replaced with Essential 8 medium, and the cells were treated with the peptide of SEQ ID NO: 1 for 2 hours.

Figure 2:
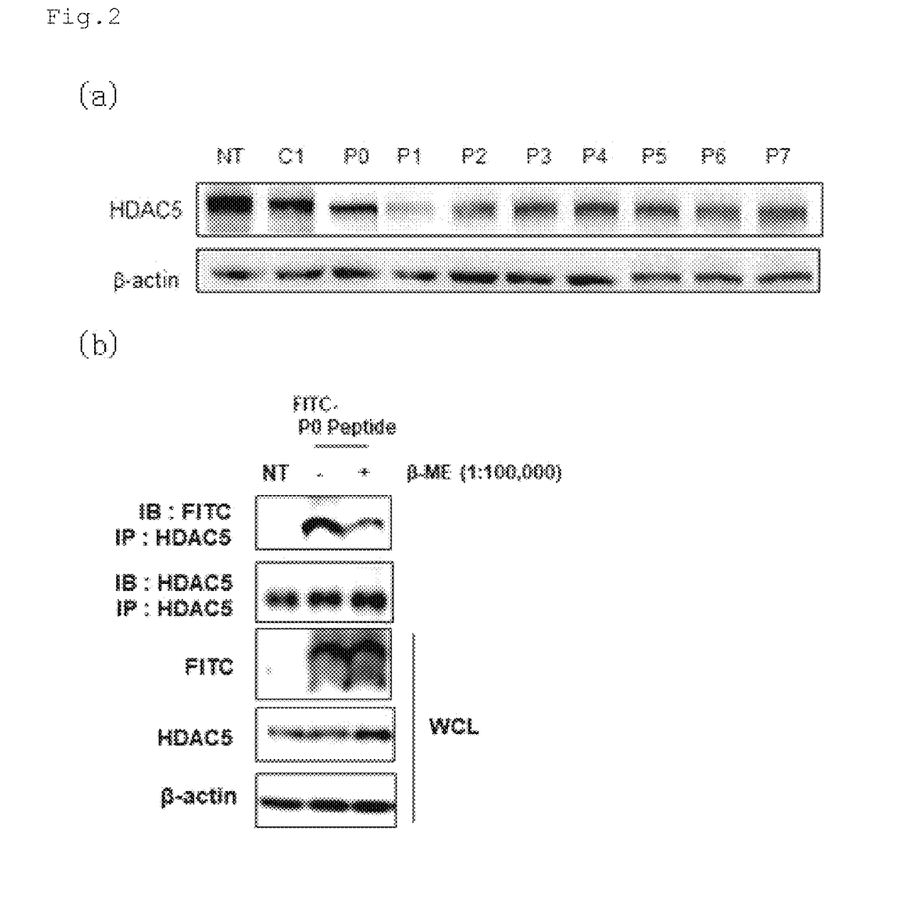
FIG. 2 in (a) shows the result of Western blot analysis of expression of intracellular HDAC5 after treating muscle precursor cells (C2C12) with the peptide of SEQ ID NO: 1 to 8 and the control peptide of SEQ ID NO: 9, and in (b) shows an immunoprecipitation result to identify binding of the peptide to intracellular HDAC5 after treating muscle precursor cells with the peptide of SEQ ID NO: 1 (SEQ ID NO: 1: P0, SEQ ID NO: 2:P1, SEQ ID NO: 3: P2, SEQ ID NO: 4: P3, SEQ ID NO: 5: P4, SEQ ID NO: 6: P5, SEQ ID NO: 7: P6, SEQ ID NO: 8: P7, SEQ ID NO: 9: C1).

Then, the binding ability to intracellular HDAC5 was identified by immunoprecipitation. The lysate harvested with RIPA buffer containing a protease inhibitor was quantified through a BCA assay. Each sample quantified with a minimum volume of 500 μl at a concentration of 1 μg/ml was collected in a microtube, 2 μg of HDAC5 first antibody was added thereto, and the mixture was reacted under rotation for 16 hours at 4° C. in a refrigerated state. 20 μl of protein A/G agarose beads were added and reacted at 4° C. for 3 hours. Then, the beads were centrifuged, washed three times with DPBS and heated at 85° C. for 5 minutes in a 2× sample buffer, and only the supernatant was obtained, followed by western blotting and identification using an FITC antibody. As a result, it was found that the peptide of SEQ ID NO: 1 binds to intracellular HDAC5 (see (a) in FIG. 2).

Muscle precursor cells (C2C12) were cultured under the same conditions as above, and the medium was replaced, and at the same time, the cells were treated with 100 μM of the peptide of each of SEQ ID NOS: 1 to 8 and 100 μM of the control peptide (SEQ ID NO: 9). On the fifth day, the expression of HDAC5 was identified by Western blotting. As a result (see (b) of FIG. 2), the groups treated with the peptides of SEQ ID NOS: 1 to 8 inhibited the expression of HDAC 5, compared to the group not treated with the peptide (NT) and the control peptide (SEQ ID NO: 9).

Test Example 3: Evaluation of Capability to Differentiate Stem Cells into Myocytes by Bifunctional Peptide Having Capability to Permeate Cells and Capability to Regenerate Muscles $3 \times 10^6$ mesenchymal stem cells were cultured in a bacterial culture dish for 3 days to form spheroids. The medium used was low-glucose DMEM with 10% FBS and 1% P/S. After 3 days, the supernatant was removed and only the spheroids were collected and seeded in a cell culture dish coated with 10 ug/ml of collagen type I for 4 days. The medium used was DMEM/F12 with 1 ng/ml TGFb (transforming growth factor beta), 1×NEAA (nonessential amino acids) and 1×ITS (insulin-transferrin selenium). After 4 days, the medium was changed to low-glucose DMEM with 2% FBS and 10 ng/ml IGF-1 (insulin growth factor-1), differentiation was further induced for 2 weeks, and muscle differentiation markers were identified. The cells were treated with 100 μM of the group not treated with peptide using only a muscle differentiation medium (NT), 100 μM of the groups treated with the peptides of SEQ ID NOS: 1 to 8 and 100 μM of the control peptide (SEQ ID NO: 9) in order to determine the efficiency of expression of the muscle differentiation markers by the peptides. The levels of gene expression of dystrophin and myogenin, as muscle differentiation markers, were measured through real-time RT-PCR. The base sequences of the PCR primers used for amplification of respective genes are as follows.

```
Myogenin
SEQ ID NO: 10: Forward primer:
5'-CTACAGGCCTTGCTCAGCTC-3'

SEQ ID NO: 11: Reverse primer:
5'-ACGATGGACGTAAGGGAGTG-3,

Dystrophin
SEQ ID NO: 12: Forward primer:
5'-GTGGGAAGAAGTAGAGGACTGTT-3'

SEQ ID NO: 13: Reverse primer:
5'-AGGTCTAGGAGGCGTTTTCC-3'
```

Figure 3:
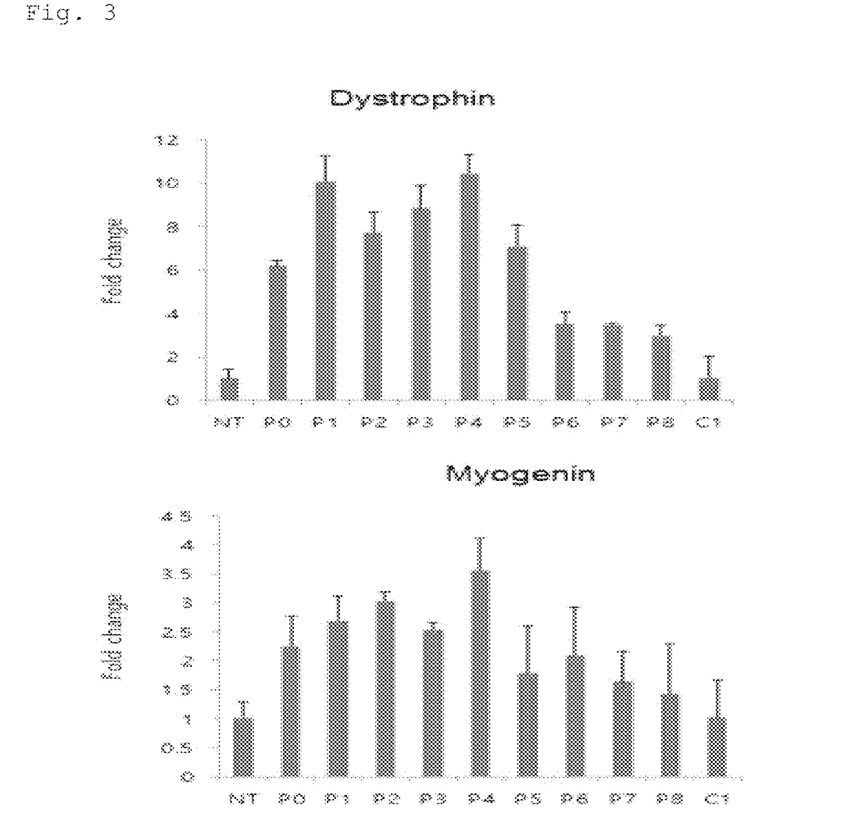
FIG. 3 shows the result of real-time RT-PCR analysis of the expression change of dystrophin and myogenin, marker proteins in muscle cells, to identify the differentiation level of stem cells into myocytes 13 days after treating mesenchymal stem cells with the peptides of SEQ ID NOS: 1 to 8 and the control peptide of SEQ ID NO: 9 (SEQ ID NO: 1: P0, SEQ ID NO: 2:P1, SEQ ID NO: 3: P2, SEQ ID NO: 4: P3, SEQ ID NO: 5: P4, SEQ ID NO: 6: P5, SEQ ID NO: 7: P6, SEQ ID NO: 8: P7, SEQ ID NO: 9: C1).

As shown in FIG. 3, the groups treated with the peptides of SEQ ID NOS: 1 to 8 exhibited an increase in gene expression of dystrophin and myogenin, and the control peptide (SEQ ID NO: 9) and the group not treated with peptide did not exhibit an increase in gene expression of muscle differentiation markers.

Figure 4:
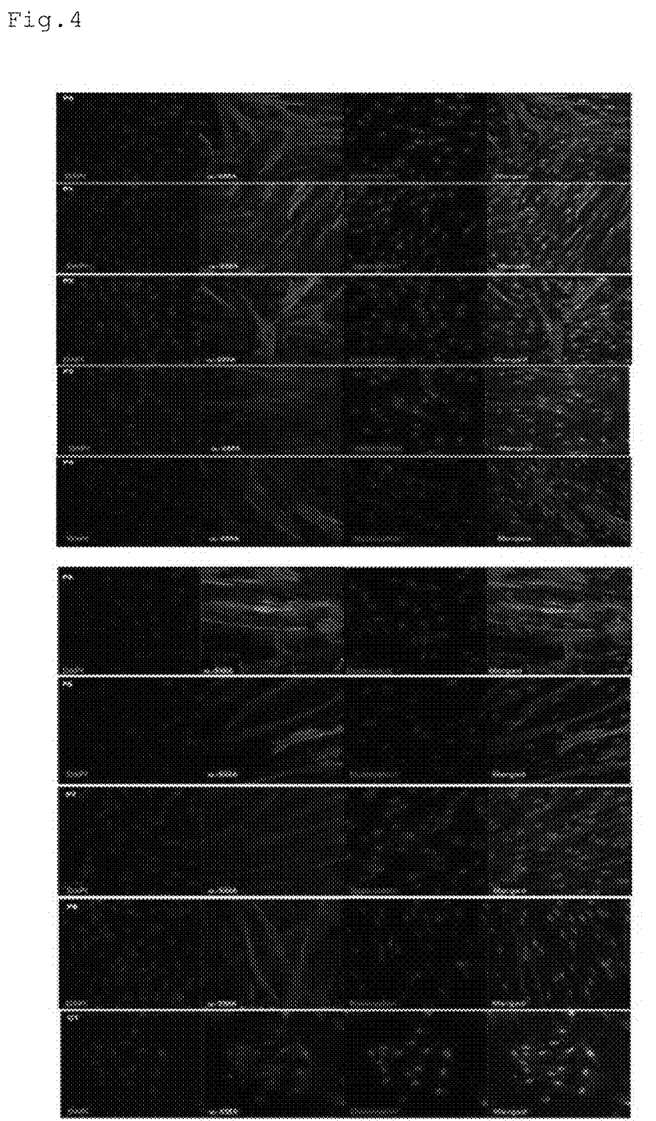
FIG. 4 shows the result of confocal microscopic analysis of the expression change of dystrophin, myogenin and SMA, marker proteins of muscle cells, to identify the differentiation level of stem cells into myocytes 13 days after treating mesenchymal stem cells (MSCs) with the peptides of SEQ ID NOS: 1 to 8 and the control peptide of SEQ ID NO: 9 (SEQ ID NO: 1: P0, SEQ ID NO: 2:P1, SEQ ID NO: 3: P2, SEQ ID NO: 4: P3, SEQ ID NO: 5: P4, SEQ ID NO: 6: P5, SEQ ID NO: 7: P6, SEQ ID NO: 8: P7, SEQ ID NO: 9: C1).

These expression markers were also measured by immunofluorescence analysis. The cultured cells were immobilized on a slide with acetone and methanol (1:1) and then washed with tris-buffered saline (TES:Sigma). Then, the cells were immobilized with a solution containing 2% bovine serum albumin (Sigma) and 5% goat serum (Sigma) for 30 minutes. Then, reaction was with DAPI, and carried out for 1 hour at room temperature using a primary antibody against a-SMA, dystrophin (Santa Cruz Biotechnology, Santa Cruz, Calif., USA). The nuclei were stained a-SMA was reacted with FITC-conjugated anti-avidin at room temperature for 30 minutes and again washed with TBS. Dystrophin was reacted with rhodamine-conjugated anti-avidin at room temperature for 30 minutes, washed again with TBS, and observed with a confocal microscope. As shown in FIG. 4, the expression of a-SMA and dystrophin was clearly observed in the group of cells treated with the peptides of SEQ ID NOs: 1 to 8, which means that the peptides had excellent myogenic differentiation and regeneration effects.

Although specific configurations of the present invention have been described in detail, those skilled in the art will appreciate that preferred embodiments of this description are given for illustrative purposes and should not be construed as limiting the scope of the present invention. Therefore, the substantial scope of the present invention is defined by the accompanying claims and equivalents thereto.

Advantageous Effects

Advantageously, the bifunctional peptide according to the present invention has a function of regenerating muscle cells and thus is useful for the prevention or treatment of diseases requiring muscle regeneration, and additionally has the capability to permeate cells and thus eliminates the necessity to adhere an additional peptide or adding another agent or drug for cell permeation of peptides, and facilitates migration, proliferation and differentiation of cells within a short period of time owing to the cell permeation capability of the peptide, thereby finally exerting an efficient muscle generation effect. Thus, the bifunctional peptide can be easily applied to various surgical regenerative treatments and can shorten the treatment period.

What is claimed is:

1. A method for treating a muscle disease, comprising administering a bifunctional peptide represented by an amino acid sequence of any one of SEQ ID NOS: 1 to 8, wherein the muscle disease is selected from the group consisting of muscular dystrophy, muscular atrophy, muscular sarcopenia, myositis, polymyositis, peripheral vascular disease, and fibrosis.

2. The method according to claim 1, wherein the peptide is a bifunctional peptide having a capability to permeate cells and a capability to regenerate muscles.

3. The method according to claim 1, wherein the peptide facilitates differentiation of stem cells into myocytes.

4. The method according to claim 1, wherein the peptide is prepared for oral administration, injection or topical implantation.

5. The method according to claim 1, wherein the peptide is administered at a dose of 0.001 to 1,000 mg per 1 kg of a body weight of a subject in need of treatment.

* * * * *

UNITED STATES PATENT AND TRADEMARK OFFICE
CERTIFICATE OF CORRECTION

PATENT NO. : 10,815,312 B2
APPLICATION NO. : 16/297864
DATED : October 27, 2020
INVENTOR(S) : Yoon Jeong Park

Page 1 of 1

It is certified that error appears in the above-identified patent and that said Letters Patent is hereby corrected as shown below:

On the Title Page

Under OTHER PUBLICATIONS, in the title of the seventh cited publication:
Kin, S., et al. ".... Collagen Sponge in a Rabbit Model" should be -- ..... Collagen Sponge Scaffold in a Rabbit Model --.

Signed and Sealed this
Twenty-second Day of December, 2020

Andrei Iancu
*Director of the United States Patent and Trademark Office*

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
```

<223> OTHER INFORMATION: bifunctional peptide

<400> SEQUENCE: 1

Gly Lys Cys Ser Thr Arg Gly Arg Lys Cys Cys Arg Arg Lys Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: bifunctional peptide

<400> SEQUENCE: 2

Gly Lys Cys Ser Thr Arg Gly Arg Lys Cys Met Arg Arg Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: bifunctional peptide

<400> SEQUENCE: 3

Gly Lys Cys Ser Thr Arg Gly Arg Lys Met Cys Arg Arg Lys Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: bifunctional peptide

<400> SEQUENCE: 4

Gly Lys Cys Ser Thr Arg Gly Arg Lys Met Met Arg Arg Lys Lys
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: bifunctional peptide

<400> SEQUENCE: 5

Gly Lys Met Ser Thr Arg Gly Arg Lys Cys Cys Arg Arg Lys Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: bifunctional peptide

<400> SEQUENCE: 6

Gly Lys Met Ser Thr Arg Gly Arg Lys Met Cys Arg Arg Lys Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: bifunctional peptide

<400> SEQUENCE: 7

Gly Lys Met Ser Thr Arg Gly Arg Lys Cys Met Arg Arg Lys Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: bifunctional peptide

<400> SEQUENCE: 8

Gly Lys Met Ser Thr Arg Gly Arg Lys Met Met Arg Arg Lys Lys
1               5                   10                  15

<210> SEQ ID NO 9
<211> LENGTH: 19
<212> TYPE: PRT
<213> ORGANISM: Artificial Sequence
<220> FEATURE:
<223> OTHER INFORMATION: Control peptide C1

<400> SEQUENCE: 9

Gly Leu Arg Ser Lys Ser Lys Lys Phe Arg Arg Pro Asp Ile Gln Tyr
1               5                   10                  15

Pro Asp Ala

<210> SEQ ID NO 10
<211> LENGTH: 20
<212> TYPE: DNA
<213> ORGANISM: Artificial Sequence
<220> FEATURE:
<223> OTHER INFORMATION: Forward primer

<400> SEQUENCE: 10
ctacaggcct tgctcagctc                                          20

<210> SEQ ID NO 11
<211> LENGTH: 20
<212> TYPE: DNA
<213> ORGANISM: Artificial Sequence
<220> FEATURE:
<223> OTHER INFORMATION: Reverse primer

<400> SEQUENCE: 11
acgatggacg taagggagtg                                          20

<210> SEQ ID NO 12
<211> LENGTH: 23
<212> TYPE: DNA
<213> ORGANISM: Artificial Sequence
<220> FEATURE:
<223> OTHER INFORMATION: Forward primer

<400> SEQUENCE: 12
gtgggaagaa gtagaggact gtt                                      23

<210> SEQ ID NO 13
<211> LENGTH: 20
<212> TYPE: DNA
<213> ORGANISM: Artificial Sequence
<220> FEATURE:
<223> OTHER INFORMATION: Reverse primer

```
<400> SEQUENCE: 13
aggtctagga ggcgttttcc                                              20
```